United States Patent [19]
Lodewijk et al.

[11] Patent Number: 4,906,756
[45] Date of Patent: Mar. 6, 1990

[54] 2-(2-NITROVINYL)THIOPHENE REDUCTION AND SYNTHESIS OF THIENO[3,2-C]PYRIDINE DERIVATIVES

[75] Inventors: Eric Lodewijk, Boulder; Hiralal N. Khatri, Louisville, both of Colo.

[73] Assignee: Syntex (U.S.A.) Inc., Palo Alto, Calif.

[21] Appl. No.: 192,274

[22] Filed: May 10, 1988

[51] Int. Cl.$^4$ .................. C07D 495/04; C07D 333/20
[52] U.S. Cl. ........................................ 546/114; 549/74
[58] Field of Search ........................... 546/114; 549/74

[56] References Cited

U.S. PATENT DOCUMENTS

| | | | |
|---|---|---|---|
| 4,051,141 | 9/1977 | Castaigne | 260/294.8 C |
| 4,078,002 | 3/1978 | Brown | 260/583 K |
| 4,127,580 | 11/1978 | Braye | 546/114 |
| 4,128,561 | 12/1978 | Braye | 260/329 AM |
| 4,174,448 | 11/1979 | Bousquet et al. | 546/114 |

FOREIGN PATENT DOCUMENTS

| | | |
|---|---|---|
| 2508456 | 12/1982 | France . |
| 61-271291A | 12/1986 | Japan . |
| 7801004 | 7/1978 | Netherlands . |
| 2166730A | 5/1986 | United Kingdom . |

OTHER PUBLICATIONS

Hydroboration—Herbert C. Brown, W. A. Benjamin, New York, pp. 247–250 (1962).
Wagner and Zook, Synthetic Org. Chem., Wiley, p. 149 (1953).
"Potentially Therapeutic Thienopyridines and Furopyridines", Maffrand et al., Eur. J. Med. Chem.--Chim. Ther., 9(5), 483–486, 1974, Chem. Abs. vol. 82, 125302z, 1975.
"Thiophene Isosters of Isoquinoline, I. On the Synthesis of Thieno[2,3-c]Pyridines and Thieno[3,2-c]Pyridines", Gronowitz et al., Arkiv for Kemi, 13(19), 217–227, 1970.

Primary Examiner—Mary C. Lee
Assistant Examiner—Bernard I. Dentz
Attorney, Agent, or Firm—David A. Lowin; Tom M. Moran

[57] ABSTRACT

An improved process for the reduction of 2-(2-nitrovinyl)thiophene to form 2-(2-thienyl)ethylamine employs a boron-containing reducing agent, preferably diborane. The 2-(2-thienyl)ethylamine produced by this process is advantageously converted to ticlopidine.

10 Claims, No Drawings

2-(2-NITROVINYL)THIOPHENE REDUCTION AND SYNTHESIS OF THIENO[3,2-c]PYRIDINE DERIVATIVES

BACKGROUND OF THE INVENTION

1. Field of the Invention

The present invention relates to processes for the synthesis of thieno[3,2-c]pyridine derivatives, particularly ticlopidine, and specifically to an improved process for reduction of 2-(2-nitrovinyl)thiophene to form 2-(2-thienyl)ethylamine.

2. Background Information

Previous technology for the preparation of ticlopidine has entailed a low yielding, labor intensive process, employing certain potentially harzardous and expensive materials. The cost of preparing ticlopidine has, therefore, been high. It has been desired to provide improved synthetic process technology that allows for a higher conversion, reduced labor usage, and the elimination of costly, potentially dangerous materials.

A variety of synthetic approaches to making ticlopidine have been described in the art, including improvements on the various steps of such synthetic processes, e.g., as described below.

Ticlopidine was first described by Castaigne in U.S. Pat. No. 4,051,141, where the synthesis thereof was accomplished by condensation of a thieno[3,2-c]pyridine with o-chlorobenzyl chloride.

Another synthetic route involved preparation of a 2-(2-thienyl)ethanol, its conversion to 2-(2-thienyl)ethyl paratoluene sulfonate and benzylation with o-chlorobenzylamine to give N-(2-chloro-benzyl)-2-(2-thienyl)ethylamine hydrochloride, which is cyclized to give ticlopidine free base, as described by Braye in U.S. Pat. No. 4,127,580.

Condensation of a 4,5,6,7-tetrahydrothieno[3,2-c]pyridine with o-chlorobenzyl chloride in the presence of a tertiary amine (triethylamine) was described in Japanese Kokai J6 1271-291A.

The benzylation of thieno[3,2-c]pyridine and NaBH$_4$ reduction of resulting quaternary salts; condensation of 4,5,6,7-tetrahydrothieno[3,2-c]pyridine with o-chlorobenzyl chloride in the presence of potassium carbonate; and benzoylation of 4,5,6,7-tetrahydrothieno[3,2-c]pyridine followed by LiAlH$_4$ reduction are described by Maffrand et al., in *Eur J. Med. Chem.-Chim. Ther.*, 9(5), 483-6 (1974).

The use of phase transfer catalysts in alkylation/benzylation reactions is known in the literature [see, e.g., Berg et al., *Acta. Chem. Scand.*, 26, 4130 (1972) and Ferris et al., *J. Org. Chem.*, 44, 173 (1979)]. Synthesis of ticlopidine under such conditions is described in UK Patent Application GB 2,166,730.

Cyclization of 2-(2-thienyl)ethylamine to 4,5,6,7-tetrahydrothieno[3,2-c]-pyridine is described by Gronowitz et al. in *Arkiv Kemi*, 13(19), 217-227 (1970).

Cyclization of N-(2-chlorobenzyl)-2-(2-thienyl)ethyl amine with formaldehyde to form ticlopidine is shown in NL 7801-004, and cyclization with dimethoxymethane is generically disclosed in U.S. Pat. No. 4,174,448 to Bousquet et al.

The electrochemical reduction of 2-(2-nitrovinyl)thiophene to give 2-(2-thienyl)ethylamine is described in UK Patent Application GB 2,013,196A.

SUMMARY OF THE INVENTION

One aspect of the present invention relates to a process employing a boron-containing reducing agent, preferably diborane, for the reduction of 2-(2-nitrovinyl)thiophene to form 2-(2-thienyl)ethylamine, the compound of Formula I.

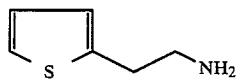

Formula I

In another aspect, the invention relates to a process for synthesis of thieno[3,2-c]pyridine derivatives of Formula II (where n is 1 or 2, and R is a phenyl or benzoyl radical optionally substituted with 1-3 halogen atoms, alkyl having 1-6 carbon atoms, alkoxy having 1-6 carbon atoms, or hydroxy or with nitro) and the pharmaceutically acceptable salts thereof, from the 2-(2-thienyl)ethylamine so-prepared.

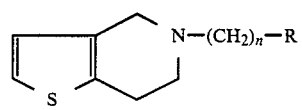

Formula II

In still another aspect, the invention relates to a process for the synthesis of ticlopidine hydrochloride (shown as Formula III, a salt within the scope of Formula II) from the 2-(2-thienyl)ethylamine so-prepared.

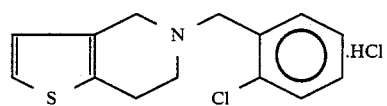

Formula III

In other aspects, the invention relates to thieno[3,2-c]pyridine derivatives made by the process of the invention, particularly ticlopidine, and to methods of treatment therewith.

DETAILED DESCRIPTION OF THE INVENTION

Definitions and General Parameters

The following definitions are set forth to illustrate and define the meaning and scope of the various terms used to describe the invention herein.

A "pharmaceutically acceptable acid addition salt" of the thieno[3,2-c]pyridine derivatives may be any salt derived from an inorganic or organic acid, e.g., ticlopidine hydrochloride. The term "pharmaceutically acceptable anion" refers to the anion of such acid addition salts. The salt and/or the anion are chosen not to be biologically or otherwise undesirable.

The anions are derived from inorganic acids, such as hydrochloric acids, hydrobromic acid, sulfuric acid (giving the sulfate and bisulfate salts), nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, salicylic acid, methanesulfonic acid, ethanesulfonic acid, p-toluenesulfonic acid and the like.

As used herein, the term "halo" refers to fluoro, bromo, chloro and iodo.

As used herein, the term "treatment" or "treating" means any treatment of a disease in a mammal, including:

(i) preventing the disease, that is, causing the clinical symptoms of the disease not to develop;

(ii) inhibiting the disease, that is, arresting the development of clinical symptoms; and/or (iii) relieving the disease, that is, causing the regression of clinical symptoms.

As used herein, the term "effective amount" means a dosage sufficient to provide treatment for the disease state being treated. This will vary depending on the patient, the disease and the treatment being effected. See, for example, U.S. Pat. No. 4,051,141 to Castaigne (the pertinent portions of which are incorporated herein by reference), for a detailed description of the anti-inflammatory activity, vaso-dilator activity, and inhibitory activity on blood plate aggregation of the thieno[3,2-c]pyridine derivatives made according to the present invention, as well as the description of toxicological and pharmacological investigations therefor.

As used herein, the terms "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, pyridine dioxane, xylene glyme, and the like]. Unless specified to the contrary, the solvents used in the reactions of the present invention are inert organic solvents.

Unless specified to the contrary, the reactions described herein take place at atmospheric pressure over a temperature range from about 10° C. to about 100° C., more preferably from about 10° C. to about 50° C., and most preferably at about room (or "ambient") temperature, e.g., about 20° C.

Isolation and purification of the compounds and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures can, of course, also be used.

Synthesis of the Compounds of Formulae I, II and III

The compounds of Formulae I, II and III are synthesized as described with reference to Reaction Schemes 1 to 3.

Reaction Scheme 1 illustrates the reduction of 2-(2-nitrovinyl)thiophene to form 2-(2-thienyl)ethylamine.

Reaction Scheme 2 illustrates the conversion of 2-(2-thienyl)ethylamine to thieno[3,2-c]pyridine derivatives by benzylation of 4,5,6,7-tetrahydrothieno[3,2-c]pyridine.

Reaction Scheme 3 illustrates an alternate synthetic route for the conversion of 2-(2-thienyl)ethylamine to thieno[3,2-c]pyridine derivatives by benzylation of 2-(2-thienyl)ethylamine followed by cyclization.

Preparation of 2-(2-thienyl)ethylamine (I)

2-(2-Nitrovinyl)thiophene (Formula 1) is commercially available from Biddle Sawyer Corporation of New York, N.Y., or from Shell's subsidiary Ward-Blenkinsop & Co., Ltd. It can be prepared according to the procedure of Gronowitz et al. [*Arkiv Kemi*, 32(19), 217–227 (1970)].

Reaction Scheme 1

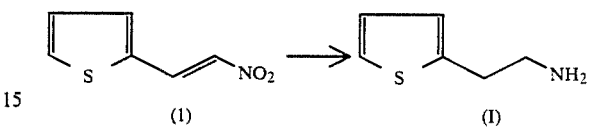

One procedure for preparing 2-(2-nitrovinyl)thiophene begins with 2-thiophenecarboxaldehyde (available from Aldrich), which is mixed in a solvent (e.g., a lower alkanol such as methanol) with nitromethane and cooled to about 0° C. An aqueous base (preferably NaOH) is added to the mixture, maintaining the temperature at about 0°–5° C. The base is neutralized with an acid (preferably HCl) to give a yellow precipitate that is filtered, washed and dried in vacuo to give 2-(2-nitrovinyl)thiophene, which is then reduced with a boron-containing reducing agent, preferably diborane.

Diborane is prepared according to methods known to those skilled in the art (e.g., the methods referenced in *The Merck Index*, 10th Ed., 2987). A presently preferred preparation is by the reaction of sodium borohydride (available from Aldrich) with an excess of boron trifluoride etherate (available from Aldrich) in a solvent (e.g., a polar solvent such as THF) by stirring in an inert atmosphere (e.g., nitrogen) at reduced temperature such as −20° to 10° C., preferably 0° to −10° C., for a period of about 2 to 6 hours, preferably about 3 to 4 hours.

As illustrated in Reaction Scheme 1, 2-(2-nitrovinyl)thiophene (Formula 1) in a solvent (e.g., a polar solvent such as THF, dioxane, or glyme; preferably THF) is slowly added to a molar excess (3-5:1) of a stirred solution of diborane in the same or a different solvent, maintaining the temperature at about 5° to 15° C., preferably 8° to 10° C. for a period of about 30 minutes to 2 hours, preferably 60 to 90 minutes. The 2-(2-nitrovinyl)thiophene/diborane mixture is stirred, maintaining a reduced temperature of about 5° to 20° C., preferably about 10° to 15° C., for about 8 to 72 hours, preferably about 18 to 40 hours.

A different solvent (e.g., a non-planar solvent such as toluene, xylene, or benzene; preferably toluene) is added and the solvents are removed by distillation until the temperature reaches 90° to 95° C. The mixture is then refluxed at the reflux temperature of the solvent used (e.g., at 90° to 93° C. using toluene) for a period of about 15 to 90 minutes, preferably about 30 to 60 minutes.

The mixture is cooled to about −20° to 20° C., preferably about −10° to 10° C., and most preferably about 0° C., followed by the slow addition of water and a dilute aqueous acid (e.g., hydrochloric acid, sulfuric acid or acetic acid; preferably a 1:5 mixture of water and 20% aqueous hydrochloric acid). The mixture is then heated to about 70° to 90° C., preferably about 80° C. for a period of about 1 to 2 hours, preferably about 90 minutes. The mixture is then cooled to about 40° to 60° C., preferably about 50° C., and the aqueous phase is separated.

The organic phase is washed with a dilute acid (e.g., hydrochloric acid, sulfuric acid or acetic acid; preferably 10% HCl). The combined aqueous layers containing the amine salt are cooled to about −5° to 10° C., preferably 0° to 5° C., basified to a pH of about 10 to 14 (e.g., by addition of NaOH, KOH, or NH₄OH; preferably NaOH); the amine is extracted into methylene chloride (or a similar solvent such as toluene, dichloroethane, or chloroform), washed and dried. Concentration of the extracts in vacuo affords 2-(2-thienyl)ethylamine (giving about an 80-94% yield of the compound of Formula I) as a pale yellow oil, which is used without further purification for the synthesis of the thieno[3,2-c]pyridine derivatives, particularly ticlopidine.

Reaction Scheme 2

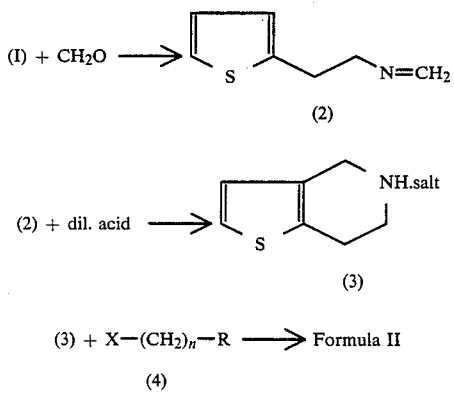

Preparation of 4,5,6,7-Tetrahydrothieno[3,2-c]pyridine (3)

4,5,6,7-Tetrahydrothieno[3,2-c]pyridine can be prepared according to the procedure of Gronowitz et al. [*Arkiv Kemi,* 13(19), 217–227 (1970)].

As illustrated in Reaction Scheme 2, a slight molar excess of formaldehyde (e.g., a 37% aqueous solution) is added dropwise with stirring to 2-(2-thienyl)ethylamine (I). The reaction mixture is stirred for about 1 to 5 hours, preferably about 3 hours, at the reflux temperature of the solvent used. After cooling to room temperature, the product is extracted, e.g., into toluene (or another solvent such as dichloromethane, chloroform, or ethyl acetate), washed and concentrated in vacuo to give the formimine of 2-(2-thienyl)ethylamine (a 90-95% yield of the compound of Formula 2).

The formimine (2) is shaken with a dilute solution of an aqueous acid (such as hydrochloric acid or sulfuric acid) or a solution of formamine (2) dissolved in an organic solvent such as THF or toluene, preferably THF, is shaken with an organic acid (such as formic acid, oxalic acid, paratoluene sulfonic acid or methane sulfonic acid; preferably methane sulfonic acid) for 3 to 10 hours, preferably about 6 hours. The mixture is then basified (e.g., with NaOH) and extracted, e.g., with methylene chloride (or another solvent). The extracts are washed and concentrated in vacuo to give 4,5,6,7-tetrahydrothieno[3,2-c]pyridine (a 80-90% yield of the compound of Formula 3).

Preparation of Formula II

Still referring to Reaction Scheme 2, a solution of 4,5,6,7-tetrahydrothieno[3,2-c]pyridine in a solvent (e.g., a polar solvent, such as THF, dichloromethane or acetonitrile; preferably THF) is added to a molar excess of a suspension of a base (e.g., a metal hydride, such as lithium hydride, 50% sodium hydride, or potassium hydride; preferably, 50% sodium hydride) in the same or a similar solvent. The mixture is stirred at a temperature of about 15° to 30° C., preferably about room temperature for about 10 minutes to about 2 hours, preferably about 30 minutes and a slight molar excess (e.g., a ratio of about 1.1 to 0.7) of an optionally substituted phenalkyl or phenacyl halide of Formula 4 [where X is halo, n is 1 or 2, and R is a phenyl or benzoyl radical optionally substituted with 1–3 halogen atoms or alkyl having 1-6 carbon atoms, alkoxy having 1-6 carbon atoms, or hydroxy or nitro, (for example the halides of Formula III in U.S. Pat. No. 4,051,141, such as 4-methoxybenzyl chloride, phenacyl bromide, or preferably o-chlorobenzyl chloride)] is added.

After stirring at about room temperature, for about 1 to 2 hours, preferably about 90 minutes, the mixture is heated, preferably to the reflux temperature of the solvent used. Another solvent (e.g., toluene, xylene, or ether; preferably toluene) is added and the mixture is further refluxed for about 2 to 48 hours, preferably for about 10 to 30 hours, most preferably about 20 hours. The mixture is then cooled to about room temperature and acidified (e.g., with dilute hydrochloric acid or acetic acid; preferably hydrochloric acid).

The organic layer separated, the aqueous layer is extracted (e.g., with toluene, dichloromethane, ethyl acetate, or i-propyl acetate; preferably toluene) and the combined aqueous layers are basified (e.g., with aqueous NaOH or solid NaOH) to a pH of about 13–14. The product is extracted, e.g., into methylene chloride (or another solvent). The extracts are washed (e.g., with water optionally including a salt solution), dried and then concentrated in vacuo to give a compound of Formula II.

When the compound of Formula 4 is o-chlorobenzyl chloride, ticlopidine free base (Formula III) is formed (about 80% yield) as a light yellow oil.

Phase Transfer Alkylation

Alternatively, the alkylation can be performed under phase transfer conditions, e.g., as described in GB 2,166,730, the pertinent parts of which are incorporated herein by reference. The 4,5,6,7-tetrahydrothieno[3,2-c]pyridine (3) and compound of Formula 4 (preferably o-chlorobenzyl chloride) are dissolved in a solvent system (preferably an aqueous:organic two-phase solvent system, the organic phase of which is immiscible with water, e.g., hydrocarbons such as benzene, toluene and xylene; and ethers such as isopropyl ether and diethyl ether; preferably toluene) combined with a phase transfer catalyst [e.g., a quaternary ammonium salt, such as trimethylbenzyl ammonium hydroxide, hydrogen sulfate tetra-n-butyl ammonium, trioctylmethyl ammonium chloride, triethylbenzyl ammonium chloride or tert-butyl ammonium iodide ("TBAI"), or a phosphonium salt, such as tetrabutyl phosphonium chloride, or a crown ether, such as 18-crown-6 or dibenzo 18-crown-6; preferably TBAI] in the presence of a base [e.g., sodium hydroxide, potassium hydroxide, lithium hydroxide, potassium carbonate, sodium carbonate, or sodium hydride; preferably sodium hydroxide] and stirred for about 24 to 72 hours, preferably about 40 hours, at room temperature. The product (75% of theoretical yield) is separated, concentrated, and purified by the usual means.

Preferred Alkylation

In a preferred alkylation procedure, 4,5,6,7-tetrahydrothieno[3,2-c]pyridine in a solvent (e.g., a polar solvent, such as THF, dichloromethane or acetonitrile; preferably 5–15% wet THF) and a compound of Formula 4 (preferably o-chlorobenzyl chloride) are added to a molar excess of a base (e.g., potassium carbonate, sodium carbonate, or lithium carbonate; preferably potassium carbonate) that has been wetted with water (about 5 to 15%, preferably about 10% of the volume charge) and the reaction mixture is refluxed until disappearance of the starting materials is confirmed by tlc (about 8 to 42 hours, preferably about 18–24 hours). The solvent is removed (by vacuum or by displacement with another solvent such as toluene), and the product is washed with water and then concentrated in vacuo. Using the preferred compound of Formula 4, ticlopidine free base (Formula III) is formed (about 90–95% yield) as a light yellow oil.

Reaction Scheme 3

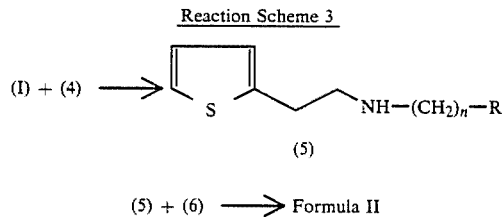

(5) + (6) ⟶ Formula II

Alternate Preparation of Formula II

Alkylation of 2-(2-thienylethylamine, Followed by Cyclization

Another alternative preparation of the compounds of Formula II is illustrated above in Reaction Scheme 3, where the compound of Formula I, prepared as described above with reference to Reaction Scheme 1, is contacted with a compound of Formula 4 under the conditions described above to give the secondary amine of Formula 5, which is in turn cyclized by contacting it with a compound identified in Reaction Scheme 3 as Formula 6 (i.e., formaldehyde, paraformaldehyde, trioxane or a compound of Formula III of U.S. Pat. No. 4,174,448, such as dimethoxymethane) under the conditions described in U.S. Pat. No. 4,174,448, the pertinent portions of which are incorporated herein by reference.

Preparation of the Salts of Formula II

Some of the compounds of Formula II may be converted to corresponding acid addition salts. The conversion is accomplished by treatment with a stoichiometric amount of an appropriate acid, such as hydrochloric acid, sulfuric acid, methanesulfonic acid, HBr, or the like (for tyclopidine the preferred acid is hydrochloric). Typically, the free base is dissolved in a polar organic solvent such as ethanol or methanol, and the acid is added in water, ethanol or methanol. The temperature is maintained at 0°–50° C. The resulting salt precipitates spontaneously or may be brought out of solution with a less polar solvent (such as toluene, ether, or ethyl acetate; preferably toluene).

Preferably, for making ticlopidine hydrochloride, about 1.3 equivalents of gaseous hydrogen chloride is bubbled into isopropanol, which is then added slowly with stirring to ticlopidine free base in toluene, maintaining the temperature below about 40° C. during the addition. The stirring is continued for about 30 to 90 minutes, preferably about 1 hour at about 45°–50° C., followed by cooling to about 5°–10° C. for about 30 to 90 minutes, preferably about 1 hour, and the ticlopidine hydrochloride precipitates. It is isolated (e.g., by centrifugation), digested (e.g., with toluene and isopropanol, or preferably with acetone), dried (e.g., at about 65° to 70° C. under vacuum), and recrystallized from a lower alkanol (e.g., methanol, ethanol or isopropanol).

The acid addition salts of the compounds of Formula II may be converted to the corresponding free bases by treating with an excess of a suitable base, such as ammonia or sodium bicarbonate, typically in the presence of aqueous solvent, and at a temperature of between 0° and 50° C. The free base form is isolated by conventional means, such as extraction with an organic solvent.

Preferred Processes and Last Steps

A preferred process for making 2-(2-thienyl)ethylamine, comprises reacting 2-(2-nitrovinyl)thiophene with a boron-containing reducing agent, preferably diborane.

A preferred process for making ticlopidine comprises the steps of:

a. reacting 2-(2-nitrovinyl)thiophene with diborane to give 2-(2-thienyl)ethylamine, and
b. converting the 2-(2-thienyl)ethylamine to ticlopidine.

In the above-described preferred process for making ticlopidine, further preferred is the process wherein the step of converting the 2-(2-thienyl)ethylamine to ticlopidine comprises the steps of:

c. contacting said 2-(2-thienyl)ethylamine with formaldehyde to give the formimine;
d. cyclizing said formimine by contacting it with an aqueous mineral acid to form 4,5,6,7-tetrahydrothieno[3,2-c]pyridine; and
e. alkylating said 4,5,6,7-tetrahydrothieno[3,2-c]pyridine to give ticlopidine, by contacting it with o-chlorobenzyl chloride under either:
   (i) phase transfer conditions, or
   (ii) preferably, by reflux with a base, most preferably potassium carbonate, using conventional alkylation conditions.

Most preferred is the above processes comprising the additional step of converting the ticlopidine made from 2-(2-thienyl)ethylamine obtained by reacting 2-(2-nitrovinyl)thiophene with a boron-containing reducing agent, to the hydrochloride salt.

Preferred Compound

The preferred compound was made by the process of the invention is 5-(2-chlorobenzyl)-4,5,6,7-tetrahydrothieno[3,2-c]pyridine, which is also known as ticlopidine. Particularly preferred is the hydrochloride salt thereof.

EXAMPLES

The following preparations and examples are given to enable those skilled in the art to more clearly understand and to practice the present invention. They should not be considered as limiting the scope of the invention, but merely as being illustrative and representative thereof.

EXAMPLE 1

Preparation of 2-(2-Nitrovinyl)thiophene

A 2 liter, 3-necked round bottom flask (adapted with mechanical stirrer, thermometer and nitrogen atmosphere) is charged with 51.6 g 2-thiophenecarboxaldehyde, 1 liter of methanol and 34.9 g of nitromethane, and cooled to 0° C. A solution of 36.0 g NaOH and 91 ml water is prepared, cooled to 5° C., and added slowly to the reaction flask, maintaining the temperature between 0° and 5° C. The reaction mixture is stirred within this temperature range for 4 hours. Again, maintaining the temperature range, 300 ml of water is added to the reaction flask.

A 3 liter 3-necked round bottom reaction flask (adapted with mechanical stirrer, thermometer and nitrogen atmosphere) is charged with 108.0 ml of concentrated hydrochloric acid and 200.0 ml of water, and cooled to 0° C. The reaction mixture from the 2 liter flask is added slowly to the 3 liter flask containing the hydrochloric acid, at such a rate as to maintain the temperature between 0° and 5° C., to form a yellow precipitate. The precipitate is filtered rapidly in a Buchner funnel, rinsed with 500 ml of water, and dried under vacuum at 40° C. for 12 hours to give the desired product.

Following the above procedure, there was obtained 51.7 g 2-(2-nitrovinyl)thiophene (72.4% T, 100.2% w/w) which was assayed by GC to be 99.98% pure.

EXAMPLE 2

Preparation of 2-(2-Thienyl)ethylamine

To a slurry of sodium borohydride (7.0 g, 0.185 mole) in THF (70 ml), cooled to −5° to −10° C. and in a nitrogen atmosphere, is slowly added boron trifluoride etherate (30 ml, 0.24 mole) maintaining the temperature between 0° to −5° C. After the addition the mixture is stirred for 3 to 4 hours at −5° to 10° C. Slowly, a solution of 2-(2-nitrovinyl)thiophene (6.0 g, 0.038 mole) in THF (60 ml) is added and the mixture is stirred for 60 to 90 minutes, maintaining the temperature between 8° to 10° C. The reaction mixture is allowed to warm to 10° to 15° C. and stirred for 2 hours, and stirring is continued for 18 to 20 hours at room temperature. The absence of starting material is confirmed by TLC. Toluene (50 ml) is added and the solvents are removed by distillation until the pot temperature reaches 60° C. Another 50 ml of toluene is added and the solvents are removed by distillation until the pot temperature reaches 90° C. The mixture is then refluxed at 90° to 93° C. for 30 to 60 minutes. After cooling to 0° to −10° C., water (20.0 ml) followed by dilute hydrochloric acid (100 ml) are slowly and carefully added. The mixture is heated to 80° C. for 90 minutes, allowed to cool to 50° C. and the aqueous phase is separated. The organic phase is washed with 50 ml of 10% HCl, the aqueous layers are combined, cooled to 0° to −5° C., and slowly basified to pH 13-14 with caustic. The aqueous phase is extracted into methylene chloride (3×100 ml) and the combined extracts are washed with 100 ml of water, dried over anhydrous magnesium sulfate, and concentrated to afford the desired product.

Following the above procedure, there was obtained 4.1 g (83.4%) 2-(2-thienyl)ethylamine as a pale yellow oil.

(b.p. 115°-130° C./20-22 mm) NMR (CDCl$_3$)δ: 6.8-7.2; (m, 3H), 2.92 (br.s, 4H), 1.28 (br.s, 2H).

EXAMPLE 3

Preparation of Ticlopidine

3A. Formimine of 2-(2-Thienyl)ethylamine

A 37% aqueous formaldehyde solution (2.7 g, 0.033 mole) is added dropwise with stirring to 3.4 g (0.027 mole) of 2-(2-thienyl)ethylamine. The reaction mixture is stirred for three hours at reflux. After cooling to room temperature, the product is extracted into toluene (2×50 ml) and toluene extracts are washed with water (50 ml) and concentrated to give the desired product.

Following the above procedure, there was obtained 3.4 g (91%) of the formimine of 2-(2-thienyl)ethylamine. NMR (CDCl$_3$) δ: 7.2-6.8 (m, 3H), 3.46 (s, 2H), 3.0-2.7 (m, 4H).

3B. 4,5,6,7-tetrahydrothieno[3,2-c]pyridine

The formimine of 2-(2-thienyl)ethylamine, prepared, for example, as described in Example 3A is shaken with 7 ml of 6N hydrochloric acid for six hours. The mixture is basified with 60 ml sodium hyroxide and extracted with 3×70 ml methylene chloride. The methylene chloride extracts are washed with water (1×50 ml) and concentrated to give the desired product.

Following the above procedure, there was obtained 3.4 g (about 100%) of crude 4,5,6,7-tetrahydrothieno[3,2-c]pyridine.

NMR (CDCl$_3$) δ: 7.06 (d, 1H), 6.72 (d, 1H), 3.9; (br.s, 2H), 3.2-2.7 (m, 4H), 2.10 (br.s, —NH).

3C. Ticlopidine Free Base

To a suspension of sodium hydride (0.42 g, 8.6 mmole) in THF (5.0 ml) is added a solution of 4,5,6,7-tetrahydrothieno[3,2-c]pyridine (1.0 g, 7.2 mmole), prepared, for example, as described in Example 3B, in THF (10 ml). The mixture is stirred under a nitrogen atmosphere at room temperature for 30 minutes and o-chlorobenzyl chloride (1.74 g, 10.8 mmole) is added. After stirring at room temperature for 90 minutes, toluene (15 ml) is added and the mixture is heated to reflux for 15 to 20 hours. Disappearance of starting material is confirmed by TLC. The mixture is then cooled to room temperature and acidified with 40 ml 1N hydrochloric acid. The organic layer is separated. The aqueous layer is extracted with 50 ml of toluene. The aqueous layer is then separated and basified with dilute aqueous sodium hydroxide to pH 13-14. The product is extracted into methylene chloride (3×40 ml). The methylene chloride extracts are washed (1×50 ml water) and (1×50 ml salt solution) then dried over anhydrous magnesium sulfate and concentrated to give the desired product.

Following the above procedure, there was obtained 1.5 g (80%) of 5-(2-chlorobenzyl)-4,5,6,7-tetrahydrothieno[3,2-c]pyridine (ticlopidine free base) as a light yellow oil.

NMR (CDCl$_3$) δ: 7.7-7.15 (m, 4H), 7.05 (d, 1H), 6.65 (d, 1H), 3.8 (s, 2H), 3.6 (s, 2H), 2.85 (br.s, 4H).

3D. Ticlopidine Hydrochloride

Gaseous HCl (0.22 g, 0.006 mole) is bubbled into 50 ml isopropanol. The resulting solution is added dropwise to ticlopidine free base (1.5 g, 0.005 mole) in 50 ml toluene, prepared, for example as described in Example 3C, maintaining the temperature below 40° C. during the addition. The reaction mixture is stirred for 1 hour, cooled to about 5°-10° C. for 1 hour, and the precipitate separated by centrifugation. An acetone slurry is made of the precipitate, brought to reflux for 1 hour, and cooled to about 5°–10° C. for 1 hour. The precipitate, ticlopidine hydrochloride (Formula III), is separated by centrifugation, dried at 65°–70° C. under vacuum, and recrystallized from methanol. (m.p. 206.5°–207.5° C.)

3E. Other Compounds of Formula II

By following the procedure of Example 3C and substituting for o-chlorobenzyl chloride the following:
m-chlorobenzyl chloride,
o-bromobenzyl bromide,
3,4,5-trimethoxybenzyl chloride,
phenacyl bromide, and
o-methoxyphenacyl bromide;
there are obtained the following respective compounds:
5-(3-chlorobenzyl)-4,5,6,7-tetrahydrothieno[3,2-c]pyridine,
5-(2-bromobenzyl)-4,5,6,7-tetrahydrothieno[3,2-c]pyridine,
5-(3,4,5,-trimethoxybenzyl)-4,5,6,7-tetrahydrothieno[3,2-c]pyridine,
5-phenacyl-4,5,6,7-tetrahydrothieno[3,2-c]pyridine, and
5-(o-methoxyphenacyl)-4,5,6,7-tetrahydrothieno[3,2-c]pyridine.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A process for making 2-(2-thienyl)ethylamine, wherein said process comprises reacting 2-(2-nitrovinyl)thiophene with a boron-containing reducing agent.

2. The process of claim 1 wherein said boron-containing reducing agent is diborane.

3. The process of claim 2 carried out in an inert organic solvent at 8° to 15° C. for 1 to 40 hours.

4. A process for making ticlopidine, said process comprising the steps of:
   a. reacting 2-(2-nitrovinyl)thiophene with diborane to give 2-(2-thienyl)ethylamine, and
   b. converting said 2-(2-thienyl)ethylamine to ticlopidine.

5. The process of claim 4 comprising the additional step of converting said ticlopidine to the hydrochloride salt.

6. The process for making ticlopidine of claim 4 wherein said step of converting said 2-(2-thienyl)ethylamine to ticlopidine comprises the steps of:
   c. contacting said 2-(2-thienyl)ethylamine with formaldehyde to give the formimine;
   d. cyclizing said formimine by contacting it with aqueous hydrochloric acid to form 4,5,6,7-tetrahydrothieno[3,2-c]pyridine; and
   e. alkylating said 4,5,6,7-tetrahydrothieno[3,2-c]pyridine to give ticlopidine, by contacting it with o-chlorobenzyl chloride under either:
      (i) phase transfer conditions, or
      (ii) by reflux with a base.

7. The process for making ticlopidine of claim 6 wherein said alkylation (step e.) comprises contacting said 4,5,6,7-tetrahydrothieno[3,2-c]pyridine with a base selected from the group including potassium carbonate, sodium carbonate and lithium carbonate, using conventional alkylation conditions.

8. The process of claim 6 comprising the additional step of converting said ticlopidine to the hydrochloride salt.

9. The process of claim 7 comprising the additional step of converting said ticlopidine to the hydrochloride salt.

10. The process of claim 2 carried out in an inert organic solvent at 5° to 20° C. for 30 minutes to 72 hours.

* * * * *